United States Patent [19]

Naegeli

[11] 4,013,711
[45] Mar. 22, 1977

[54] AZULENE COMPOUNDS

[75] Inventor: Peter Naegeli, Wettingen, Switzerland

[73] Assignee: Givaudan Corporation, Clifton, N.J.

[22] Filed: Nov. 3, 1975

[21] Appl. No.: 628,304

Related U.S. Application Data

[62] Division of Ser. No. 363,207, May 23, 1973, Pat. No. 3,935,253.

[30] Foreign Application Priority Data

June 5, 1972 Switzerland .................. 8265/72

[52] U.S. Cl. .................. 260/488 B; 260/476 C; 260/586 F
[51] Int. Cl.² .............. C07C 69/02; C07C 69/06; C07C 69/14; C07C 69/78
[58] Field of Search .................. 260/476 C, 488 B

[56] References Cited

OTHER PUBLICATIONS

Takeda et al., Tetrahedron, vol. 13, pp. 308–318 (1961).

Primary Examiner—Jane S. Myers
Attorney, Agent, or Firm—Thomas Cifelli, Jr.

[57] ABSTRACT

Novel compounds of formula

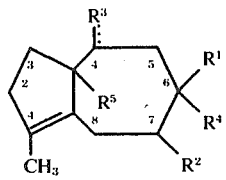

wherein $R^1$ represents a lower alkenyl group or $R^{11}$, or taken together with $R^4$ an oxo group; $R^{11}$ represents hydrogen or a lower alkyl group; $R^2$ represents hydrogen or a lower alkyl group; $R^3$ represents methyl or methylene; $R^4$ represents hydroxy or a loweralkoxy, lower alkenyloxy, loweralkoxyloweralkyl or acyloxy group and $R^5$ represents hydrogen or, when simultaneously $R^3$ represents methyl and $R^1$ represents $R^{11}$, taken together with $R^4$ a 3α,6-epoxide group, and 1,8α-dihydro-derivatives of compounds of formula I wherein $R^3$ represents methyl and $R^5$ represents hydrogen.

6 Claims, No Drawings

AZULENE COMPOUNDS

The use of said compounds as odorants and also processes for their preparation are disclosed.

This is a division of application Ser. No. 363,207 filed May 23, 1973, now U.S. Pat. No. 3,935,253.

DETAILED DESCRIPTION OF THE INVENTION

The invention relates to novel compounds having the general formula

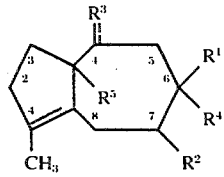

I wherein
- $R^1$ represents a lower alkenyl group or $R^{11}$, or taken together with $R^4$ an oxo group;
- $R^{11}$ represents hydrogen or a lower alkyl group;
- $R^2$ represents hydrogen or a lower alkyl group;
- $R^3$ represents methyl or methylene;
- $R^4$ represents hydroxy or a lower alkoxy, lower alkenyloxy, loweralkoxyloweralkyl or acyloxy group and
- $R^5$ represents hydrogen or, when simultaneously $R^3$ represents methyl and $R^1$ represents $R^{11}$, taken together with $R^4$ a 3α,6-epoxide group, and 1,8a-dihydro derivatives of compounds of formula I wherein $R^3$ represents methyl and $R^5$ represents hydrogen.

Formula I encompasses inter alia compounds of the formulae

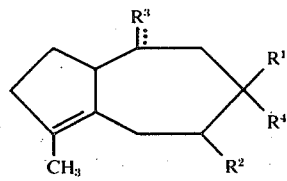

II and

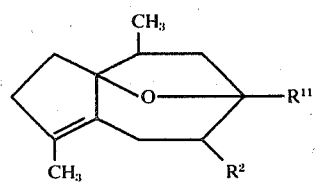

III wherein $R^1$, $R^2$, $R^3$, $R^4$ and $R^{11}$ have the significance given above.

Formula II and dihydro derivatives thereof in accordance with the invention encompass inter alia compounds of following formulae IV-XII

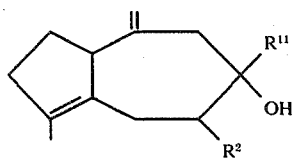

IV

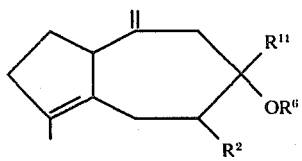

V

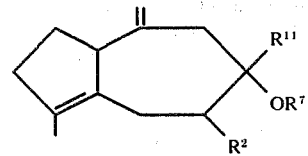

VI

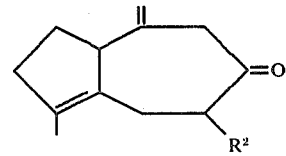

VII

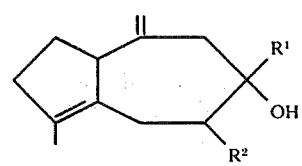

VIII

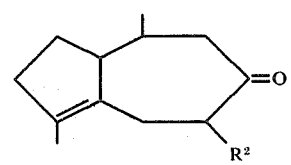

IX

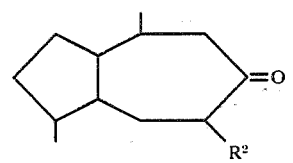

X

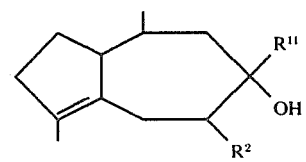

XI

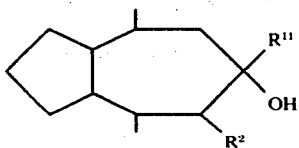

XII wherein $R^1$, $R^2$ and $R^{11}$ have the meanings given above, $R^6$ represents acyl and $R^7$ represents loweralkyl, loweralkenyl or loweralkoxyloweralkyl.

The expression "lower" used in connection with the foregoing definitions includes groups having from 1 to 6 carbon atoms. Alkyl and alkenyl groups, for example in alkenyloxy or alkoxyalkyl residues, may be branched or straight-chain. The expression "acyl" includes residues of aliphatic and aromatic carboxylic acids such as formic, acetic, propionic, butyric, valeric or benzoic acid.

The compounds of formula I in accordance with the invention and 1,8a-dihydro derivatives of compounds I in which $R^3$ represents methyl and $R^5$ represents hydrogen, can be manufactured by cyclising a 3-isopropenyl-1-methyl-1-cyclopentene having the general formula

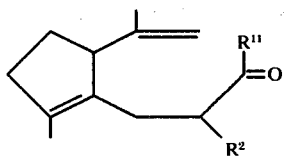

XIII in an organic solvent and in the presence of a Lewis acid to give a compound of the formula

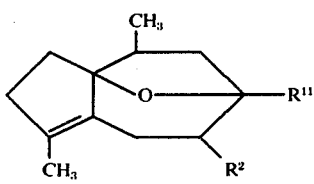

III or

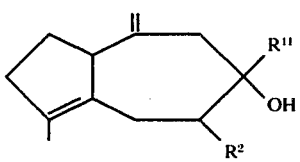

IV and where appropriate a. esterifying a compound of formula IV so obtained to give a compound of the formula

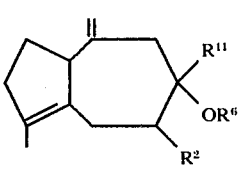

V wherein $R^6$ represents an acyl residue, or b. esterifying a compound of formula IV so obtained to give a compound of the formula

VI

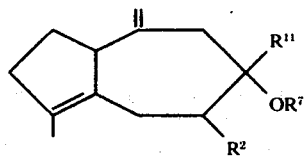

wherein $R^7$ represents an alkyl, alkenyl or alkoxyalkyl group or c. oxidising a compound of formula IV so obtained to give a compound of the formula

VII

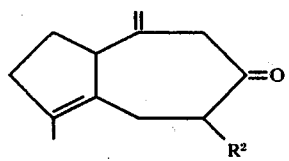

and, where appropriate, reacting the ketone so obtained with a Grignard compound of the formula $R^1$-MgHal wherein $R^1$ is as defined above and Hal represents chlorine or bromine and subsequently hydrolysing to a yield compound of the formula

VIII and where appropriate etherifying or esterifying a compound of formula VIII so obtained or hydrogenating a ketone of formula VII to give a compound having the formula

IX or

-continued

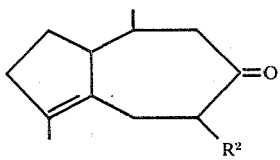     X or d. hydrogenating a compound having the formula IV so obtained to give a compound having the formula

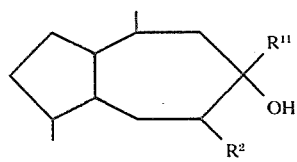     XI or

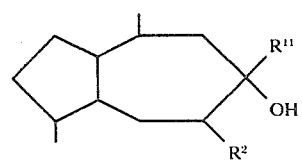     XII and where appropriate, esterifying or etherifying the compound of formulae XI or XII so obtained, wherein in the formulae given $R^1$, $R^2$ and $R^{11}$ have the meanings given above in connection with formula I.

Organic solvents which may conveniently be used for the cyclisation of a 3-isopropenyl-1-methyl-1-cyclopentene (XIII) to a compound of formula IV include apolar aliphatic and aromatic hydrocarbons such as e.g. pentane, hexane, cyclohexane, benzene and toluene. Preferred solvents for the cyclisation of a compound of formula XIII to a compound of formula III include nitrated aliphatic hydrocarbons, especially nitromethane and nitropropane. The reaction is preferably effected under anhydrous conditions. The solvent should therefore be as dry as possible, however small amounts of water or of hydrolysis products of the Lewis acids, such as for example HCl may be present. Preferred Lewis acids include titanium and tin tetrachloride. The cyclisation is conveniently carried out under an inert gas atmosphere (nitrogen, argon) and at temperatures from below room temperature up to room temperature. The especially preferred temperature range for the cyclisation yielding compounds of formulae IV is about 0°–5°, that for cyclisations yielding compounds of formulae III about −40° to −20° C. Oxidation of a compound of formula IV to a compound of formula VII can likewise be effected in conventional manner for example a preferred oxidising agent is chromic acid in pyridine or in an acidic medium (Jones reagent).

The conversion of the ketone of formula VII into a compound of formula VIII by reaction with a Grignard compound and also the hydrogenation of compounds of formulae IV and VII to compounds of formulae XI or XIII or IX or X may be effected in a conventional manner. The partial hydrogenation of compounds of formula VII or IV to compounds of formula IX or XI can be effected catalytically with the uptake of one equivalent of hydrogen, for example in the presence of platinum oxide or palladium, while the compounds of formula X or XII can be obtained either directly from the compounds of formula VII or IX by catalytic hydrogenation, for example with a noble metal catalyst in an inert organic solvent, or alternatively from the already partially hydrogenated compounds IX or XI.

Etherification or esterification of a compound of formula IV which may be effected after the cyclisation reaction as well as etherificaton or esterification of a compound of formula VIII may be effected by conventional methods.

The compounds of formula I in accordance with the invention are characterised by particular odoriferous qualities and can accordingly be used as odorants in perfumery, for example for the manufacture or for the odoriferous modification of odorant compositions such as perfumes, perfume bases etc by addition of olfactorily-perceptible amounts, e.g. 0.1–10 wt.%, to a mixture of known odorants. The compounds can also be used for the perfuming of commercial and cosmetic products of all kinds, e.g. of solid and liquid detergents, synthetic washing agents, aerosols, soaps, creams, lotions etc. e.g. in concentrations of about 0.002–0.1 wt.%.

The starting compounds of formula XIII may be prepared by reacting a compound of the formula

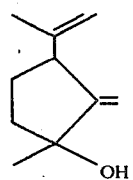     XIV in the presence of an acid catalyst with an enol ether of the formula

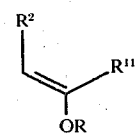     XV or a corresponding ketal of the formula

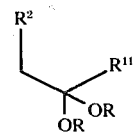     XVI wherein
  R represents a lower alkyl residue and
  $R^2$ and $R^{11}$ have the meanings given above.

The invention will now be illustrated with reference to the following Examples.

EXAMPLE 1

To a solution, cooled to 0°, of 57 g of 3-isopropenyl-1-methyl-2-(3-oxopropyl)-1-cyclopentene in 3 l of absolute benzene and 800 ml of absolute ether were added dropwise under a nitrogen atmosphere within 30 minutes 900 ml of a 0.5 M solution of tin tetrachloride in benzene. The mixture was stirred for a further 30 minutes at 5°, whereby it became red coloured, then treated at 0° with saturated sodium carbonate solution up to an alkaline reaction and suction filtered. The benzene solution was washed with saturated sodium carbonate solution and water, dried with anhydrous sodium sulphate and evaporated under reduced pressure. The crude product obtained was fractionated on a short column with the addition of 2 g of anhydrous potash. There were obtained 41 g (yield 72%) of 6-hydroxy-1-methyl-4-methylen-2,3,3a, 4,5,6,7,8-octahydroazulene; b.p.$_{0.5}$ 90°–92°; n$_d^{20}$ = 1.5233; IR(film):$\nu_{max}$ = 3450, 3090, 1640, 1450, 1440, 1380, 1200, 1155, 1098, 1080, 1060, 1030, 942, 890, 775 cm$^{-1}$. The compound has a flowery, camphorous, woody odour.

EXAMPLE 2

To a solution, cooled to 0°, of 19.2 g of 2-(2-formyl-propyl)-3-isopropenyl-1-methyl-1-cyclopentene in 1500 ml of absolute benzene and 300 ml of absolute ether were added under a nitrogen atmosphere and vigorous stirring 300 ml of a 0.5 M benzene tin tetrachloride solution. The colourless solution was stirred for a further 30 minutes at 0° to 5° and then treated with an excess of cold saturated sodium carbonate solution. After extraction with ether, the organic phase was washed with sodium carbonate solution and water, dried with magnesium sulphate and evaporated under reduced pressure. There were obtained 20.5 g of an oily crude product which, after distillation under a pressure of 0.005 mm Hg, yielded 17 g of pure 6-hydroxy-1,7-dimethyl-4-methylene-2,3,3a, 4,5,6,7,8-octahydroazulene; b.p.$_{0.005}$ ca 70°; IR(film):$\nu_{max}$ =3550/3500, 3090, 1635, 1450, 1435, 1375, 1320, 1190, 1160, 1145, 1100, 1060, 1040, 1030, 998, 972, 948, 925, 900, 775 cm$^{-1}$. The compound has a camphorous, woody odour.

EXAMPLE 3

To a solution, cooled to 0°, of 10 g of 2-(2-formyl-3-methylbutyl)-3-isopropenyl-1-methyl-1-cyclopentene in 800 ml of absolute benzene and 200 ml of absolute ether were added under a nitrogen atmosphere and vigorous stirring 150 ml of 0.5 -M benzene tin tetrachloride solution. The mixture was stirred for a further 30 minutes at 6° and treated with an excess of saturated ice-cold sodium carbonate solution. After extraction with ether, the organic phase was washed with sodium carbonate solution and water, dried with magnesium sulphate and evaporated under reduced pressure. There were obtained 11.2 g of a yellow oil which, after distillation, yielded 9.2 g of pure 6-hydroxy-7-isopropyl-1-methyl-4-methylen-2,3,3a, 4,5,6,7,8-octahydroazulene; b.p.$_{0.01}$ 76°–77°; IR(film):$\nu_{max}$ = 3550/3460, 3080, 1635, 1455, 1438, 1382, 1365, 1325, 1195, 1160, 1030, 900 cm$^{-1}$. The substance has a woody, camphorous odour.

EXAMPLE 4

500 mg of platinum oxide were pre-hydrogenated in 300 ml of ethanol. After addition of 2.14 g of 6-hydroxy-1-methyl-4-methylen-2,3,3a, 4,5,6,7,8-octahydroazulene, the mixture was hydrogenated until hydrogen was no longer taken up. The reaction mixture was filtered, the filtrate evaporated and the crude product distilled under reduced pressure in a bulb-tube. There were obtained 1.3 g of pure 6-hydroxy-1,4-dimethyl-2,3,3a, 4,5,6,7,8-octahydroazulene; b.p.$_{0.001}$ ca 85°; IR(film):$\nu_{max}$ 3380, 1460, 1440, 1095, 1078, 1035/30, 985/75, 940 cm$^{-1}$. The substance has a woody, flowery, fresh green odour.

EXAMPLE 5

3.6 g of 6-hydroxy-1,4-dimethyl-2,3,3a, 4,5,6,7,8-octahydroazulene were hydrogenated in 25 ml of ethanol with 500 mg of palladium-on-carbon (10%). The reaction mixture was filtered, the filtrate evaporated and distilled under reduced pressure in a bulb-tube. There were obtained 2.5 g of 6-hydroxy-1,4-dimethyl-perhydroazulene; b.p.$_{0.005}$ ca 82°; IR(film):$\nu_{max}$=3360, 1460, 1375, 1030, 975 cm$^{-1}$. The compound has a fresh, woody, earthy odour somewhat reminiscent of vetiver.

EXAMPLE 6

A solution, cooled to −10°, of 26.7 g of 6-hydroxy-1-methyl-4-methylen-2,3,3a, 4,5,6,7,8-octahydroazulene in 1500 ml of acetone was treated dropwise within 30 minutes with 65 ml of Jones reagent (172 mM CrO$_3$). The mixture was poured on the excess ice-cold bicarbonate solution and exhaustively extracted with ether. The organic phase was washed with bicarbonate solution and water, dried with anhydrous magnesium sulphate and concentrated under reduced pressure. The crude product which was obtained in the form of a yellow oil, was fractionated under reduced presdure and yielded 20.5 g (yield 77%) pure 1-methyl-4-methylen-6-oxo-2,3,3a, 4,5,6,7,8-octahydroazulene; b.p.$_{0.005}$ 62°–65°; IR(film)$\nu_{max}$ = 3090, 1708, 1640, 1450/38, 1345, 1322, 1305, 1262, 1240, 1195, 1140, 1108, 950, 900, 800 cm$^{-1}$. The compound has a herb-like, camphorous, terpin oil-like odour.

EXAMPLE 7

528 mg of 1-methyl-4-methylen-6-oxo-2,3,3a, 4,5,6,7,8-octahydroazulene were hydrogenated in 20 ml of ethyl acetate wit the aid of 200 mg of palladium-on-calcium carbonate (5%): After hydrogen uptake was completed the mixture was filtered off from the catalyst, the filtrate concentrated under reduced pressure and distilled. There was obtained pure 1,4-dimethyl-6-oxo-2,3,3a, 4,5,6,7,8-octahydroazulene, b.p.$_{0.06}$ 60°; IR(film):$\nu_{max}$ = 1700, 1450, 1378, 1250, 1190 cm$^{-1}$. The compound has a woody, earthy, camphorous odour.

EXAMPLE 8

176 mg of 1-methyl-4-methylen-6-oxo-2,3,3a,4,5,6,7,8-octahydroazulene were hydrogenated in 15 ml of ethanol with 175 mg of palladium-on-carbon (5%). After hydrogen uptake was completed the mixture was filtered off from the catalyst, the filtrate evaporated and distilled in vacuum. There was obtained pure 1,4-dimethyl-6-oxo-perhydroazulene; b.p.$_{0.05}$ 60°; IR(film):$\nu_{max}$ = 1700, 1460, 1375, 1335, 1250, 1180, 980, 850 cm$^{-1}$. The compound has a camphorous, herby, woody odour.

EXAMPLE 9

A solution, cooled to −10°, of 1.10 g of 6-hydroxy-7-isopropyl-1-methyl-4-methylen-2,3,3a,4,5,6,7,8-octahydroazulene (isomer A) in 50 ml of acetone was treated within 10 minutes with 2 ml of Jones reagent (5.3 mM CrO$_3$) and the reaction mixture obtained then poured on to ice-cold bicarbonate solution. Extraction with ether, washing the extracts with bicarbonate solution and water, drying with sodium sulphate, concentration and distillation under reduced pressure yielded 990 mg (yield 90%) of 7-isopropyl-1-methyl-4-methylen-6-oxo-2,3,3a,4,5,6,7,8-octahydroazulene (isomer A) in the form of a colourless oil; b.p.$_{0.01}$ ca 75°; IR(-film):$\nu_{max}$ = 3100, 1708, 1642, 1460, 1440, 1390, 1370, 1255, 1205, 1140, 1090, 1062, 1005, 970, 900, 800 cm$^{-1}$. The compound has a sweet, spicy, woody odour. In analogous manner there were obtained from 1.10 g of the B-isomer of 6-hydroxy-7-isopropyl-1-methyl-4-methylen-2,3,3a,4,5,6,7,8-octahydroazulene, 890 g (yield 81%) of the B-isomer of the corresponding 6-oxo-octahydroazulene; b.p.$_{0.01}$ ca 75°; IR(film):$\nu_{max}$ =1390, 1710, 1642, 1470/60/40, 1390, 1370, 1265, 1180, 1092, 1062, 1000, 970, 900 cm$^{-1}$. The compound has a fresh woody, slighly spicy, camphorous odour.

EXAMPLE 10

To a Grignard solution, prepared from 6.0 g of magnesium chips in 600 ml of absolute ether and 35.4 g of methyl iodide, was added dropwise a concentrated ethereal solution of 9.68 g of 1 methyl-4-methylen-6-oxo-2,3,3a,4,5,6,7,8-octahydroazulene. The mixture was heated under reflux for 3 hours, cautiously treated with excess ammonium chloride solution and extracted with ether. The ethereal phase was washed with bicarbonate solution and water, dried with magnesium sulphate and concentrated under reduced pressure. The crude 6-hydroxy-1,6-dimethyl-4-methylene-2,3,3a,4,5,6,7,8-octahydroazulene (11 g), which was obtained in the form of a yellow oil, was fractionated under high vacuum, resulting in a separation of the two epimeric alcohols.

A much better separation of the two epimers is, however, achieved by chromatography of the entire fraction (9.95 g = 94% yield; b.p.$_{0.005}$ 50°–60°) on 25-times amount of Florisil (magnesium silicate gel) with hexane and and hexane/ether (95:5). Epimer A: b.p.$_{0.05}$ ca 60°; IR(film):$\nu_{max}$ =3600/3550, 3120, 1640, 1445, 1385, 1335/25, 1260, 1248, 1175, 1125, 1062, 978, 960, 945, 910/900, 860, 780 cm$^{-1}$. The compound has a woody, spicy, camphorous odour. Epimer B: m.p. 54°; IR(film):$\nu_{max}$ = 3400, 3120, 1645, 1460/50, 1382, 1150/40, 1115, 1070, 1050, 965, 900, 770 cm$^{-1}$. The compound has a spicy, slightly musty odour reminiscent of vetiver.

EXAMPLE 11

To a Grignard solution, prepared from 1 g of magnesium chips activated with 1 g of iodine, 5 ml of 2-bromopropene and about 100 ml of tetrahydrofuran, were added over 10 minutes 1.76 g of 1-methyl-4-methylen-6-oxo-2,3,3a,4,5,6,7,8-octahydroazulene. The mixture was stirred vigorously for 30 minutes, cooled to 0° and treated with excess ice-cold ammonium chloride solution. The mixture was then extracted with ether, the organic extract washed with carbonate solution and water, dried over magnesium sulphate and concentrated under reduced pressure. The crude product (2.6 g), which was obtained in the form of a yellow oil, was distilled under high vacuum and yielded 1.6 g (yield 76%) of pure 6-hydroxy-6-isopropenyl-1-methyl-4-methylen-2,3,3a,4,5,6,7,8-octahydroazulene; b.p.$_{0.1}$ ca 100° IR(film): $\nu_{max}$ =3550, 3090, 1640, 1450/40, 1378, 1330, 1220, 1165, 1105, 1038, 900/895, 780 cm$^{-1}$. The compound has a woody, slightly camphorous, somewhat spicy odour.

EXAMPLE 12

To a solution of vinyl magnesium bromide in tetrahydrofuran, prepared from 1.2 g of magnesium chips activated with iodine and 8 ml of vinyl bromide, was added dropwise over 10 minutes a solution of 1.76 g of 1-methyl-4-methylen-6-oxo-2,3,3a,4,5,6,7,8-octahydroazulene in 10 ml of tetrahydrofuran. After 1 hours stirring under reflux, the mixture was treated with excess cold ammonium chloride solution and extracted with ether. The organic phase was washed neutral with water, dried and concentrated under reduced pressure. There were obtained 2.4 g of a yellow oily crude product, which was chromatographed on 30-fold the amount of Florisil (magnesium silicate gel) with hexane. Yield 1.75 g (80 %) of pure 6-hydroxy-1-methyl-4-methylene-6-vinyl-2,3,3a,4,5,6,7,8-octahydroazulene; b.p.$_{0.05}$ ca 60°; IR(film): $_{max}$ = 3600/3550, 3120, 1640, 1460, 1445, 1415, 1385, 1335, 1255, 1230, 1175, 1135, 1105, 1075, 1038, 1980, 930, 910, 860, 780 cm$^{-1}$. The substance has a flowery, slightly musty odour slighly cineol-like.

EXAMPLE 13

8.9 g of 6-hydroxy-1-methyl-4-methylene-2,3,3a,4,5,6,7,8-octahydroazulene were heated under reflux for 16 hours in 150 ml of absolute benzene with 3.6 g of sodium hydride (50% in paraffin oil). After addition of 9.8 ml of diethyl sulphate at 10°, the reaction mixture was stirred for a further 8 hours at reflux, poured on to ice-cold 20% citric acid solution and extracted with ether. The ethereal extract was washed with bicarbonate solution and water, dried and concentrated under reduced pressure. There were obtained 10.3 g of an oily crude product which was fractionated under high vacuum. The fraction (8.25 g = 80% yield) passing over at a pressure of 0.01 mm Hg between 59 and 64° was pure 6-ethoxy-1-methyl-4-methylen-2,3,3a,4,5,6,7,8-octahydroazulene; IR(film):$\nu_{max}$ =3090, 1642, 1455/1440, 1370, 1345, 1125/1105/1095/1080, 1025, 890, 768 cm$^{-1}$. The compound smells fresh, green, flowery, woody, spicy.

EXAMPLE 14

In analogous manner to Example 13 there was prepared from 6-hydroxy-1-methyl-4-methylen-2,3,3a,4,5,6,7,8-octahydroazulene and dimethyl sulphate, 1-methyl-4-methylene-6-methoxy-2,3,3a,4,5,6,7,8-octahydroazulene; b.p.$_{0.05}$ ca 60°; IR(-film):$\nu_{max}$ =3090, 1640, 1455, 1440, 1380/65/55, 1240, 1195/85/75, 1140, 1105/1100, 1020, 890, 770/65 cm$^{-1}$. The substance has a woody, camphorous odour.

EXAMPLE 15

To a solution, cooled to −25°, of 7.68 g of 3-isopropenyl-1-methyl-2-(3-oxobutyl)-1-cyclopentene in 600 ml of nitromethane were added with stirring over of 7 minutes 120 ml of a 0.5-M solution of tin tetrachloride in nitromethane. The mixture was stirred for a further 5 minutes at −25° and then treated immediately with excess saturated bicarbonate solution. After extraction with ether, washing the organic phase so obtained with bicarbonate solution and water, drying with anhydrous sodium sulphate and removal of the solvent under reduced pressure, there were obtained 7.2 g of a yellow crude product which was distilled with addition of a small amount of dry potash. There were obtained 5.4 g (yield 70 %) of pure 3a,6-epoxy-1,4,6-trimethyl-2,3,3a, 4,5,6,7,8-octahydroazulene; b.p.$_{0.007}$ ca 70°; IR(film):$\nu_{max}$=1450, 1375, 1355, 1320, 1250/35, 1105, 1080/75, 985, 950, 930, 895, 885/75 cm$^{-1}$. The odour of the compound is camphorous, woody, sweet.

The same reaction, performed in benzene at temperatures above room temperature, yielded, after chromatography of the crude product on Florisil (magnesium silicate gel), the epimeric 3a,6-epoxy-1,4,6-trimethyl compound as the main product; b.p.$_{0.005}$ ca 55°; $\nu_{max}$=1460/1450, 1380, 1360, 1335/1325, 1290, 1255, 1240, 1195, 1130, 1110, 1088, 990, 975, 935, 890 cm$^{-1}$. This compound smells woody, cineol-like.

EXAMPLE 16

A solution of 3.56 g of 6-hydroxy-1-methyl-3-methylen-2,3,3a,4,5,6,7,8-octahydroazulene in 75 ml of absolute benzene was stirred for 15 hours duration at 45° with 1.44 g of sodium hydride (50% paraffin paste, purified by washing with benzene). 2.42 g of chlorodimethyl ether were added dropwise at this temperature, whereupon the temperature rose to 60°. After 20 hours stirring at reflux, the mixture was treated at 0° with an excess of 20% citric acid solution and extracted with ether. The ethereal phase was washed with water, dried, filtered through 40 g of Florisil (magnesium silicate gel) and concentrated under reduced pressure. The yellow oily crude product (3.9 g) was purified by chromatography on 30 times the amount of silica gel. By elution with methylene chloride pure 6-methoxymethyl-1-methyl-4-methylen-2,3,3a,4,5,6,7,8-octahydroazulene (2.15 g = 0% yield) was obtained and separated from a dimeric ether and the starting material; b.p.$_{0.03}$ 82°; IR(film):$\nu_{max}$=3120, 1650, 1450, 1385/75/60, 1300, 1240, 1215, 1155, 1108, 1090, 1050, 1025, 930, 900, 770 cm$^{-1}$. The odour of the compound is, on the one hand, sweet, flowery, in the direction of lavender, on the other hand, spicy, sweet, slightly tarragon, basil-like.

EXAMPLE 17

To a solution, cooled to −40°, of 3.3 g of 2-(2-formyl-3-methylbutyl)-3-isopropenyl-1-methyl-1-cyclopentene in 225 ml of nitromethane were added 45 ml of a 0.5-M solution of tin tetrachloride in nitromethane. The reaction mixture became intensely yellow in colour and an initially resulting precipitate dissolved again. The mixture was treated immediately with excess 2-N sodium carbonate solution and extracted with ether. After washing, the ethereal phase was dried in a conventional manner and the solvent was removed. Distillation under a high vacuum yielded 2.6 g of crude 3a,6-epoxy-7-isopropyl-1,4-dimethyl-2,3,3a,4,5,6,7,8-octahydroazulene in the form of a colourless oil which could be separated by chromatography on 40 times the amount of Florisil (magnesium silicate gel) with hexane/ether (19:1) into two pairs of epimers (A and B). Epimer A: b.p.$_{0.01}$ ca 75°; IR(film):$\nu_{max}$ =1465/40, 1380, 1345, 1245, 1162, 1125, 1108, 1080, 1050, 995, 965, 945, 910, 880 cm$^{-1}$. The odour is camphorous, woody. Epimer B: b.p.$_{0.01}$ ca 80° IR(film):$\nu_{max}$ =1465/35, 1380, 1340, 1295, 1245, 1200/1195, 1170, 1145, 1110, 1060, 1030, 1000, 990, 950, 925, 910, 878 cm$^{-1}$. The odour is camphorous, dull.

EXAMPLE 18

9.6 g of 6-hydroxy-1,6-dimethyl-4-methyl-2,3,3a,4,5,6,7,8-octahydroazulene in 300 ml of absolute benzene were heated to reflux for 15 hours with 4.8 g of sodium hydride (50% paraffin-containing paste, purified by washing with benzene). Then 95 ml of freshly distilled dimethyl sulphate were added at 40°. The mixture was stirred at reflux for a further 7 hours, cooled to 5°, treated with 20% citric acid solution and extracted with ether. The ethereal phase was washed with bicarbonate solution and water, dried in a conventional manner and concentrated under reduced pressure. The oily residue so obtained (12.5 g) was loaded onto 125 g of silica gel and by elution with hexane there were obtained 7.65 g (74%) of 6-methoxy-1,6-dimethyl-4-methylen-2,3,3a,4,5,6,7,8-octahydroazulene which was then distilled in high vacuum; b.p.$_{0.02}$ ca 55°; IR(film):$\nu_{max}$ =3090, 1640, 1450/40, 1370, 1252, 1120, 1080, 890, 835, 765/55 cm$^{-1}$. The compound has a camphorous, woody odour.

EXAMPLE 19

In analogous manner to Example 18 there were obtained from 2.0 g of 6-hydroxy-1,7-dimethyl-4-methylen-2,3,3a,4,5,6,7,8-octahydroazulene in 50 ml of absolute benzene with 960 mg of sodium hydride and 1.9 ml of dimethyl sulphate, 1.6 g (75%) of pure 6-methoxy-1,7-dimethyl-4-methylen-2,3,3a,4,5,6, 7,8-octahydroazulene; b.p.$_{0.01}$ ca 65°; IR(film):$\nu_{max}$ =3090, 1642, 1455, 1438, 1375, 1362, 1200, 1140, 1100, 1040, 1025, 972, 950, 892 cm$^{-1}$. The compound smells camphorous, ester-like, woody.

EXAMPLE 20

To a solution of 17.8 g of 6-hydroxy-1-methyl-4-methylen-2,3,3a,4,5,6,7,8-octahydroazulene in 25 ml of pyridine were added dropwise at 0° 25 ml of acetic anhydride. After 40 hours stirring at room temperature, the slightly brown solution was poured on to ice. The mixture was extracted with ether, the IR(KBr):$\nu\lambda$ extract washed successively with cold 2-N hydrochloric acid, saturated bicarbonate solution and water, dried in a conventional manner and concentrated under reduced pressure. The crude product so obtained (20 g) was taken up in a small amount of pentane. By crystallization there were firstly obtained 13.3 g (60.5%) of 6-acetoxy-1-methyl-4-methylen-2,3,3a,4,5,6,7,8-octahydroazulene. By distillation of the mother liquor there was obtained a further 6.65 g (30.3%) of crystalline acetate. M.p. 55°; IR(film):$\nu_{max}$ =3080, 1730, 1640, 1450/40/30, 1375, 1365, 1300, 1260/50, 1225, 1158, 1110, 1055, 1025, 992, 960, 920, 900/895, 865, 845, 795, 770, 695 cm$^{-1}$. The compound has a flowery, rose-violet-like, faintly woody odour.

EXAMPLE 21

A solution of 2.5 g of 6-hydroxy-1-methyl-4-methylen-2,3,3a,4,5,6,7,8-octahydroazulene in 5 ml of pyridine and 50 ml of methylene chloride was treated at −10° with 1.73 ml of propionyl chloride. After 3 hours stirring, the solution was poured on to ice and worked up in a conventional manner. After distillation of the crude product under high vacuum, there were obtained 3.15 g (96%) of pure 1-methyl-4-methylene-6-propionyloxy-2,3,3a,4,5,6,7,8-octahydroazulene; b.p.$_{0.05}$ 65°–70°; IR(film):$\nu_{max}$ = 1380, 1730, 1640, 1460, 1440, 1375, 1340, 1270, 1190, 1158, 1080, 1018, 895 cm$^{-1}$. The compound has a woody, spicy, balsamic, slightly earthy odour.

EXAMPLE 22

2.67 g of 6-hydroxy-1-methyl-4-methylen-2,3,3a,4,5,6,7,8-octahydroazulene were treated at 0° firstly with half of a mixture of 4.08 g of acetic anhydride, 1.84 g of formic acid and 37 mg of pyridine. The mixture was stirred for 24 hours at room temperature and with exclusion of light. Then the other half of the reagent was added and the mixture stirred for further 24 hours. The solution was poured on to a mixture of ice and sodium carbonate and worked up in a conventional manner. The crude product so obtained (3.18 g) was distilled under high vacuum and yielded 2.70 g (87%) of pure 6-formyloxy-1-methyl-4-methylen-2,3,3a,4,5,6,7,8-octahydroazulene; b.p.$_{0.005}$ 50°; IR(-film):$\nu_{max}$ = 3120, 1728, 1645, 1460/45, 1190/82, 1015/1000, 905/900 cm$^{-1}$. The compouond smells woody, cedar-like, slightly ionone-like.

EXAMPLE 23

A solution of 2.0 g of 6-hydroxy-1,6-dimethyl-4-methylen-2,3,3a,4,5,6,7,8-octahydroazulene in 5 ml of pyridine and 50 ml of methylene chloride was treated at −10° with 1.1 ml of acetyl chloride. The mixture was left to stand overnight at room temperature, then poured on to ice and worked up in a conventional manner. The crude product (3.1 g) which was obtained in the form of a brown oil, was chromatographed on 50 times the amount of silica gel. By elution with hexane/ether (19:1) there was obtained pure 6-acetoxy-1,6-dimethyl-4-methylen-2,3,3a,4,5,6,7,8-octahydroazulene; b.p.$_{0.01}$ ca 70°; IR(film):$\nu_{max}$=3090, 1735, 1640, 1445, 1368, 1270/50/30, 1095, 1065, 1020, 905/900 cm$^{-1}$. The compound has a flowery odour with a woody undertone.

EXAMPLE 24

A solution of 1.536 g of 6-hydroxy-1,7-dimethyl-4-methylen-2,3,3a,4,5,6,7,8-octahydroazulene in 2.5 ml of pyridine was treated with 2 ml of acetic anhydride and the mixture left to stand for 40 hours at room temperature. The reaction mixture was poured on to ice and worked up in a conventional manner. The crude product obtained (2g) was chromatographed on 50 times the amount of silica gel. By elution with hexane/ether (20:1) there was obtained 6-acetoxy-1,7-dimethyl-4-methylen-2,3,3a,4,5,6,7,8-octahydroazulene (yield 80%); b.p.$_{0.01}$ ca 65°; IR(film):$\nu_{max}$=3090, 1735, 1640, 1450/38, 1378, 1245, 1162/58, 1140, 1100, 1025, 985, 950.42, 895, 770 cm$^{-1}$. The compound has a tenacious, woody, flowery odour.

EXAMPLE 25

To a solution, cooled to −35°, of 4.45 g of 3-isopropenyl-1-methyl-2-(3-oxopropyl)-1-cyclopentene in 300 ml of absolute nitromethane were added dropwise under a nitrogen atmosphere 75 ml of a 0.5 molar benzene tin tetrachloride solution. During the reaction the temperature of the reaction mixture rose to about −25°. The mixture was then treated at this temperature with 2% soda solution in excess and extracted with ether. The ethereal extract was washed with water till neutral dried in a conventional manner and concentrated; 4.15 g of a red oily product being obtained. Vacuum distillation yielded 1 g of pure 3a,6-epoxy-1,4-dimethyl-2,3,3a,4,5,6,7,8-octahydroazulene; b.p.$_{0.01}$ ca 80°; IR(film):$\nu_{max}$ =1460, 1440, 1375, 1345, 1328, 1310, 1242, 1180, 1110, 1080, 1070, 1050, 1035, 1002, 980, 940, 925, 910, 875, 770 cm$^{-1}$. By chromatography on Kieselgel the product obtained by distillation can be readily obtained in still higher purity. The compound has a woody, camphorous terpene oil-like odour.

EXAMPLE 26

Odorant composition (fougère type).

Example 26

| Odorant composition (fougere type). | |
|---|---|
| | Parts by weight |
| Lavender oil | 200 |
| Bergamotte oil | 100 |
| Petitgrain oil Paraguay | 30 |
| Undecanal (10% in phthalic acid diethyl ester) | 10 |
| Dodecanal (10% in phthalic acid diethyl ester | 20 |
| Geranium oil Bourbon | 20 |
| Ylang-Ylang oil | 20 |
| Jasmin absolu synthetic | 30 |
| Geraniol pure | 30 |
| Vetiver oil Bourbon | 20 |
| α-Ionone | 80 |
| α-Methylionone | 50 |
| 4-Tert.-butyl-2,6-dimethyl-3,5-dinitro-acetophenone | 50 |
| 4-Tert.-butyl-3-methoxy-2,6-dinitrotoluene | 30 |
| Coumarin | 70 |
| Patchouli oil | 20 |
| Mousse de Chene soluble | 20 |
| Resinoid Labdanum | 10 |
| Sandalwood oil East Indian | 20 |
| Isobutylsalicylate | 20 |
| Phenylethyl alcohol | 100 |
| 6-Acetoxy-1-methyl-4-methylen-2,3,3a,4,5,6,7,8-octahydroazulene | 50 |
| | 1000 |

EXAMPLE 27

Odorant composition I (Invented note, slightly flowery theme with woody-spicy foundation).

Example 27

| Odorant composition I (Invented note, slightly flowery theme with woody-spicy foundation). | |
|---|---|
| | Parts by weight |
| Bergamotte oil | 110 |
| Lemon oil Italian | 50 |
| Petitgrain oil Paraguay | 50 |
| Lavender oil | 50 |
| α-Methylbenzylacetat | 20 |
| Rhodinol 70 Givaudan | 50 |
| Baccartol Givaudan | 50 |
| p.Tert.-butyl-α-methylhydro-cinnamaldehyde | 20 |
| Undecanal (10% in phthalic acid diethyl ester) | 10 |
| 2-Methylundecanal (10% in phthalic acid diethyl ester) | 20 |
| cis-3-Hexenylbutyrate | 5 |
| Isoraldeine Givaudan | 50 |
| Vetiveryl acetate | 100 |
| Fluve Odorante absolu (20% in phthalic acid diethyl ester) | 150 |
| Sandela Givaudan | 100 |
| Ambreine pure Givaudan | 20 |
| Coumarin | 25 |
| Calamus oil | 15 |
| Eugenol | 5 |
| Jasmin absolu synthetic | 40 |
| 6-Hydroxy-1,1,6-dimethyl-4-methyln-2,3,3a,4,5,6,7,8-octahydroazulene | 60 |
| | 1000 |

EXAMPLE 28

Odorant composition (lavender type)

Example 28

| Odorant composition (lavender type) | |
|---|---|
| | Parts by weight |
| Coumarin | 5 |
| Tonka beans resinoid | 15 |
| Ethylene-brassilate | 20 |
| Oil of thyme red (10% in phthalic acid diethyl ester) | 10 |
| Cyclamen aldehyde (10% in phthalic acid diethyl ester) | 25 |
| Undecylenaldehyde (1% in phthalic acid diethyl ester) | 30 |
| Isoraldeine Givaudan | 25 |
| Ethyllinalyl acetate | 60 |
| Bergamotte oil Reggio | 50 |
| Lavender oil 22/24 | 80 |
| p-Tert.-butylcyclohexyl acetate | 100 |
| Menthanyl acetate | 100 |
| Lavender oil 38/40 | 400 |
| 3a,6-Epoxy-7-isopropyl-1,4-dimethyl-2,3,3a,4,5,6,7,8-octahydroazulene | 80 |
| | 1000 |

What is claimed is:
1. A compouond of the formula

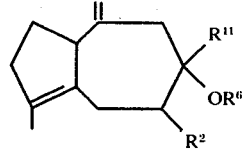

wherein $R^2$ represents hydrogen or lower alkyl,
$R^6$ represents the acyl residue of a member selected from the group consisting of formic acid, acetic acid, propionic acid butyric acid and benzoic acid and $R^{11}$ represents hydrogen or lower alkyl.

2. 1-Methyl-4-methylen-6-acetoxy-2,3,3a,4,5,6,7,8-octahydroazulene.

3. 1-Methyl-4-methylen-6-propionyloxy-2,3,3a,4,5,6, 7,8-octahydroazulene.

4. 1-Methyl-4-methylen-6-formyloxy-2,3,3a,4,5,6,7,8-octahydroazulene.

5. 1,6-Dimethyl-4-methylen-6-acetoxy-2,3,3a,4,5,6,7,8-octahydroazulene.

6. 1,7-Dimethyl-4-methylen-6-acetoxy-2,3,3a,4,5,6,7,8-octahydroazulene.

* * * * *